United States Patent
Bruemmer-Prestley et al.

(10) Patent No.: US 6,503,239 B1
(45) Date of Patent: *Jan. 7, 2003

(54) REFASTENABLE ABSORBENT ARTICLE EXHIBITING IMPROVED BODY FIT

(75) Inventors: Mary Anne Bruemmer-Prestley, Appleton, WI (US); Sarah Jane Marie Freiburger, Kaukauna, WI (US); Nefetari Edris Bordain, Dunwoody, GA (US); Suzanne Marie Schmoker, Oshkosh, WI (US); Russell Evan Thorson, Appleton, WI (US); Keith Joseph Renard, Oshkosh, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 2 days.

This patent is subject to a terminal disclaimer.

(21) Appl. No.: 09/637,432

(22) Filed: Aug. 11, 2000

Related U.S. Application Data (60) Provisional application No. 60/150,327, filed on Aug. 23, 1999.

(51) Int. Cl.$^7$ ................................................. A61F 13/15
(52) U.S. Cl. .......................... 604/385.29; 604/385.01; 604/391
(58) Field of Search ............... 604/385.01, 385.21, 604/385.24, 385.27, 385.28, 385.29, 391, 392, 396

(56) References Cited

U.S. PATENT DOCUMENTS

| | | |
|---|---|---|
| 4,205,679 A | 6/1980 | Repke et al. |
| 4,573,987 A | 3/1986 | Lamb, Jr. |
| 4,699,621 A | 10/1987 | Stevens et al. |
| 4,747,846 A | 5/1988 | Boland et al. |
| 4,834,736 A | 5/1989 | Boland et al. |
| 4,906,243 A | 3/1990 | Dravland |
| 5,370,634 A | * 12/1994 | Ando et al. ............... 604/385.1 |

(List continued on next page.)

FOREIGN PATENT DOCUMENTS

| | | |
|---|---|---|
| DE | 197 32 551 A1 | 2/1999 |
| EP | 0 321 985 A2 | 6/1989 |

(List continued on next page.)

Primary Examiner—Aaron J. Lewis
Assistant Examiner—Jamisue Webb
(74) Attorney, Agent, or Firm—Thomas J. Connelly; Scott A. Baum (57) ABSTRACT

A refastenable disposable absorbent article is disclosed having a front portion, a back portion and a crotch portion. The crotch portion connects the front portion to the back portion. The front portion has a central section including first and second side edges. First and second lateral sections are releasably attached to the central section and each lateral section has an outward edge. The front portion also has a first end and a second end. The back portion has first and second side edges and first and second ends. The back portion is divided into a first section and a second section. The first section has a length $L_2$ measured perpendicularly from the first end of the back portion to a line drawn parallel thereto. Multiple elastic strands extend transversely across the first section from the first side edge to the second side edge. The second section has a length $L_3$ measured perpendicularly from the second end to the line drawn parallel to the first end whereby a ratio $L_2/L_3$ is established which ranges from between about 0.1 to about 2. The absorbent article further includes a liquid permeable liner secured to at least one of said front, back or crotch portions and an absorbent core positioned below the liner. Each of the outward edges of the first and second lateral sections of the front portion are secured to one of the first and second side edges of the back portion to form a pant-like article having a waist opening and a pair of leg openings.

20 Claims, 4 Drawing Sheets

U.S. PATENT DOCUMENTS

| | | | |
|---|---|---|---|
| 5,527,302 A | * 6/1996 | Endres et al. | 604/385.1 |
| 5,745,922 A | 5/1998 | Rajala et al. | |
| 5,817,087 A | * 10/1998 | Takabayashi et al. | 604/385.2 |
| 5,957,908 A | * 9/1999 | Kline et al. | 604/386 |
| 6,098,203 A | 8/2000 | Rajala et al. | |
| 6,110,157 A | * 8/2000 | Schmidt | 604/385.01 |
| 6,142,986 A | 11/2000 | Lord et al. | |
| 6,312,420 B1 | 11/2001 | Sasaki et al. | |

FOREIGN PATENT DOCUMENTS

| | | |
|---|---|---|
| EP | 0 412 579 A1 | 2/1991 |
| EP | 0 433 951 A2 | 6/1991 |
| EP | 0 450 541 A2 | 10/1991 |
| EP | 0 682 928 A1 | 11/1995 |
| FR | 2 443 831 | 7/1980 |
| GB | 2 244 422 A | 12/1991 |
| GB | 2 288 313 A | 10/1995 |
| GB | 2 294 865 A | 5/1996 |
| GB | 2 308 290 A | 6/1997 |
| WO | WO 95/00096 | 1/1995 |
| WO | WO 96/11657 | 4/1996 |
| WO | WO 97/22318 | 6/1997 |
| WO | WO 97/36566 | 10/1997 |

* cited by examiner

REFASTENABLE ABSORBENT ARTICLE EXHIBITING IMPROVED BODY FIT

This application claims the benefit of Provisional Application No. 60/150,327, filed Aug. 23, 1999.

FIELD OF THE INVENTION

This invention relates to a refastenable absorbent article exhibiting improved body fit. More specifically, this invention relates to a refastenable disposable absorbent article sized to have certain ratios between certain sections that improve body fit and reduce the likelihood of fluid leakage.

BACKGROUND OF THE INVENTION

Today, various disposable absorbent articles exist which are designed to absorb and retain body fluid and/or excrement. Examples of such articles include incontinence products such as pants, briefs and undergarments, baby diapers, feminine care menstrual pants, training pants, etc. While most of these articles perform satisfactorily for their intended purpose, some are difficult to remove from the body of the wearer. Many do not have a refastenable mechanism that allows the article to be easily adjusted during use or be easily removed from the wearer's body before the product is permanently discarded while maintaining an underwear like fit. Some of today's commercially available products do not conform well to the human body and this poor fit increases the likelihood of fluid leakage while the product is being worn. Therefore, there remains a need for a refastenable, disposable absorbent article that will provide improved fit to the human body and reduce the likelihood of fluid leakage.

Now, a refastenable absorbent article has been invented which is sized to have predetermined ratios between certain sections so as to improve body fit and reduce the likelihood of fluid leakage.

SUMMARY OF THE INVENTION

Briefly, this invention relates to a refastenable absorbent article having a front portion, a back portion and a crotch portion. The crotch portion connects the front portion to the back portion. The front portion has a central section including first and second side edges. First and second lateral sections are releasably attached to the central section and each lateral section has an outward edge. The front portion also has a first end and a second end. The back portion has first and second side edges and first and second ends. The back portion is divided into a first section and a second section. The first section has a length $L_2$ measured perpendicularly from the first end of the back portion to a line drawn parallel thereto. Multiple elastic strands extend transversely across the first section from the first side edge to the second side edge. The second section has a length $L_3$ measured perpendicularly from the second end to the line drawn parallel to the first end whereby a ratio $L_2/L_3$ is established which ranges from between about 0.1 to about 2. The absorbent article further includes a liquid permeable liner secured to at least one of said front, back or crotch portions and an absorbent core positioned below the liner. Each of the outward edges of the first and second lateral sections of the front portion are secured to one of the first and second side edges of the back portion to form a pant-like article having a waist opening and a pair of leg openings.

The general object of this invention is to provide a refastenable absorbent article exhibiting improved body fit. A more specific object of this invention is to provide a refastenable disposable absorbent article sized to have certain ratios that improve body fit and reduce the likelihood of fluid leakage.

Another object of this invention is to provide a refastenable absorbent article that is easy to manufacture, is relatively inexpensive and is easy to use.

A further object of this invention is to provide a refastenable absorbent article that provides the wearer with a choice of how to apply and/or remove the absorbent article, i.e. pull the article up around the wearer's torso versus refasten the article around the wearer's torso.

Still another object of this invention is to provide a refastenable absorbent article that can easily be adjusted to conform to a wearer's body.

Other objects and advantages of the present invention will become more apparent to those skilled in the art in view of the following description and the accompanying drawings.

DETAILED DESCRIPTION OF THE PREFERRED EMBODIMENTS

Figure 1:
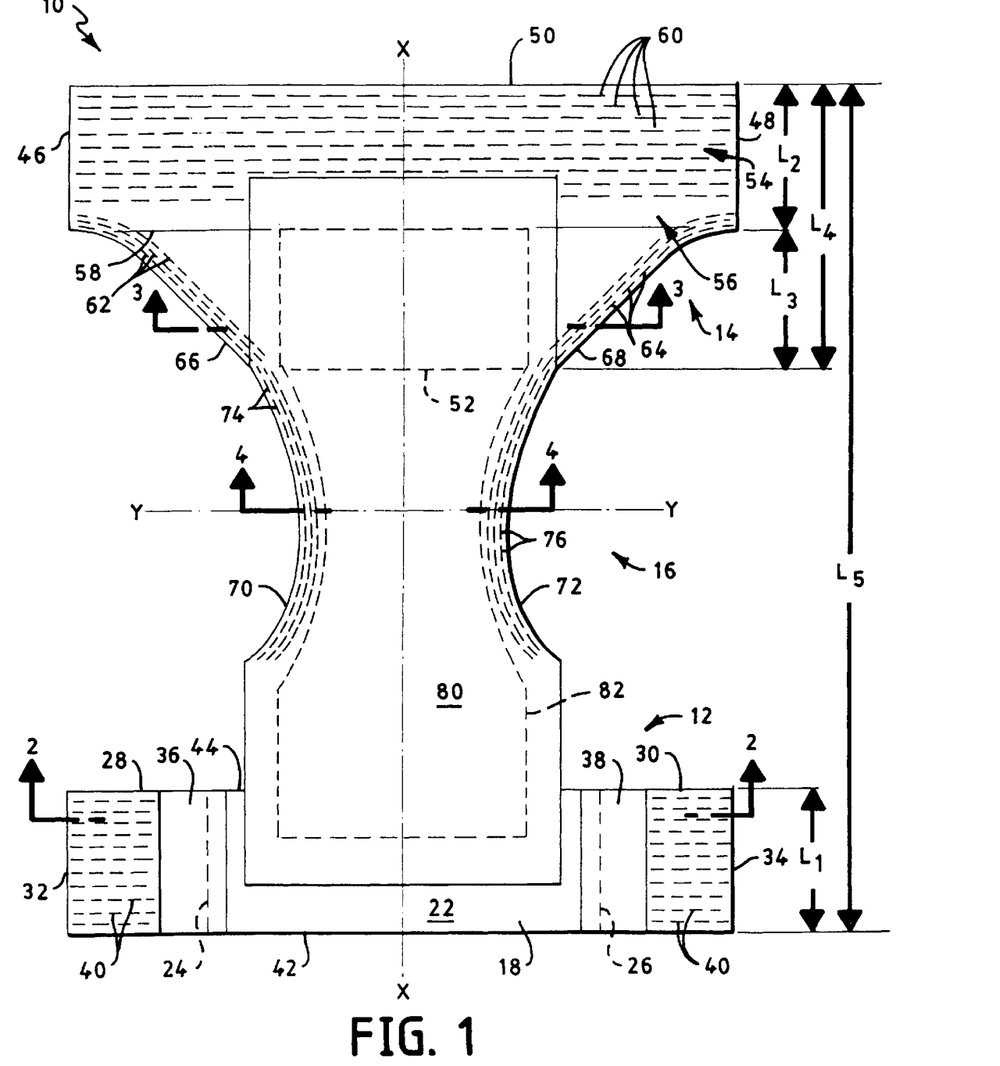
FIG. 1 is a top plane view of a refastenable absorbent article shown in a pre-assembled flat configuration.
Figure 2:
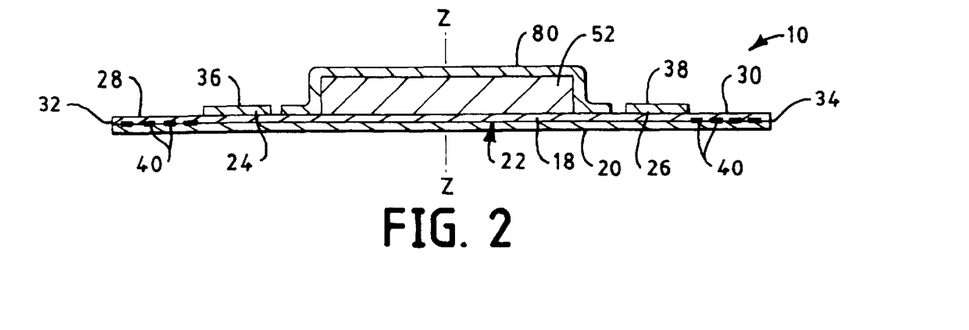
FIG. 2 is a cross-sectional view of FIG. 1 taken along line 2—2.

Referring to FIGS. 1 and 2, a refastenable absorbent article 10 is shown. The absorbent article 10 is preferably disposable and has a longitudinal central axis X—X, a transverse central axis Y—Y and a vertical central axis Z—Z. The absorbent article 10 includes a front portion 12, a back portion 14 and a crotch portion 16. The crotch portion 16 connects the front portion 12 to the back portion 14. The front, back and crotch portions 12, 14 and 16 can be formed from a single piece of material or from two or more pieces of material. Each of the front, back and crotch portions 12, 14 and 16 can be a single layer of material or be formed as a laminate from two or more layers. As depicted, the front, back and crotch portions 12, 14 and 16 are shown as a laminate having an upper layer 18 and a lower layer 20. The upper layer, which is closest to the body of the wearer can be liquid permeable or liquid-impermeable. A thermoplastic film can be used to make the upper layer 18 liquid-impermeable. The lower layer 20 can also be liquid permeable or liquid-impermeable. Preferably, the lower layer 20 is liquid permeable and is formed from a soft material such as a non-woven. Spunbond is a non-woven material manufactured by Kimberly-Clark Corporation that is soft and pliable and functions well as the lower layer 20.

The front portion 12, which will contact the front of a wearer's torso in use, includes a central section 22 with first and second side edges 24 and 26, respectively. The front portion 12 also has first and second lateral sections 28 and 30, respectively, each of which are positioned adjacent to one of the first and second side edges 24 and 26. Each of the first and second lateral sections, 28 and 30 respectively, has an outer edge 32 and 34. Each of the first and second lateral sections 28 and 30 is releasably attached to the central section 22 by a fastener 36 and 38. Each of the fasteners 36 and 38 is depicted as a separate piece of material that joins each lateral section 28 and 30 to the central section 22. The fasteners 36 and 38 can be hook materials that releasably attach to the upper layer 18 that is formed as a loop material. Alternatively, the fasteners 36 and 38 can be loop materials that releasably attach to the upper layer 18 that is as a hook material. It is also possible to secure a separate piece of hook or loop material to the upper layer 18 to which the fasteners 36 and 38 will attach. The fasteners 36 and 38 can also include one or more frangible bonds, intermittent bonds, breakable bonds, or other similar type of structure. When such bonds are present, there will not be a need for a separate piece of material as is shown in FIGS. 1 and 2. Likewise, other types of fasteners can also be employed, including glue, adhesives, co-adhesives, as well as mechanical fasteners, such as buttons and corresponding buttonholes, etc. Other fasteners are known to those skilled in the art.

It should be noted that the lateral sections 28 and 30 preferably contain elastic 40 to provide them with extendible properties. Alternatively, the lateral sections 28 and 30 can be formed from a material that exhibits elastomeric properties. When individual elastic members are utilized, the elastic 40 can be in the form of elongated strands, strips, bands, tape etc. and can have various configurations. The elastic 40. can be formed from rubber, polyurethane or other elastomeric materials. A suitable material is LYCRA® that is commercially available from the E.L. Du Pont De Nemours and Company. LYCRA® is a trademark of E.L. Du Pont De Nemours and Company having an office in Wilmington, Delaware.

The elastic 40 can include two or more members positioned between the upper and lower layers 18 and 20 and held in place by glue, an adhesive or some other type of binder. Preferably, the elastic 40 is in the form of multiple strands arranged in parallel rows relative to one another. Other arrangements for the elastic 40 can also be used.

Returning again to FIGS. 1 and 2, the front portion 12 further has a first end 42 and a second end 44. A length $L_1$ represents the actual distance between the first end 42 and the second end 44. The length $L_1$ should be equal to or greater than about 2 inches (about 5 cm). Preferably, for an adult size garment, the length $L_1$ should range from between about 3 inches to about 7 inches (about 7.6 cm to about 18 cm). Most preferably, for an adult size garment, the length $L_1$ should range from between about 6 inches to about 7 inches (about 15 cm to about 18 cm). The significance of the dimension $L_1$ will be explained shortly.

Figure 3:
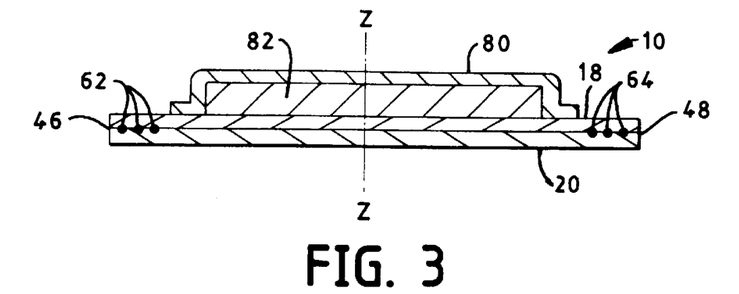
FIG. 3 is a cross-sectional view of FIG. 1 taken along the line 3—3.

Referring to FIGS. 1 and 3, the absorbent article 10 also includes the back portion 14 that will contact the back portion of a wearer's torso in use. The back portion 14 has first and second side edges 46 and 48, respectively, and first and second ends, 50 and 52 respectively. The back portion 14, as explained above, is depicted as a laminate having an upper layer 18 and a lower layer 20. The upper layer, which is closest to the body of the wearer can be liquid permeable or liquid-impermeable. Preferably, it is liquid permeable. The back portion 14 is divided into a first section 54 and a second section 56. The first section 54 has a length $L_2$ measured perpendicularly from the first end 50 to a line 58 drawn parallel thereto. The length $L_2$ should be equal to or greater than about 2 inches (about 5 cm). Preferably, for an adult size garment, the length $L_2$ should range from between about 3 inches to about 7 inches (about 7.6 cm to about 18 cm). Most preferably, for an adult size garment, the length $L_2$ should range from between about 6 inches to about 7 inches (about 15 cm to about 18 cm).

The first section 54 can be formed from an elastic material, an elastic composite or it can contain elastic 60. "Stretch bonded laminate" is an elastic material that can be used to form the first section 54. Stretch bonded laminate is manufactured by Kimberly-Clark Corporation having an office at 401 North Lake Street, Neenah, Wis. 54956. The elastic 60 can be in the form of elongated elastic strands, ribbons, bands, strips, etc. which extend transversely across the first section 54 from the first side edge 46 to the second side edge 48. Preferably, there are at least six elastic strands 48 contained in the first section 44. The number of elastic strands 60 can vary from two to about fifty. Preferably, there are from between about ten to about forty elastic strands 60. The elastic 60 functions to cause the back portion 14 of the absorbent article 10 to securely contact the back torso of the wearer and prevent fluid leakage from occurring at or about the waist opening.

The second section 56 of the back portion 14 has a length $L_3$ measured perpendicularly from the second end 52 to the line 58 drawn parallel thereto. The length $L_3$ should be equal to or greater than about 1 inch (about 2.5 cm). Preferably, for an adult size garment, the length $L_3$ should range from between about 3 inches to about 10 inches (about 8 cm to about 25 cm). Most preferably, for an adult size garment, the length $L_3$ should range from between about 4 inches to about 8 inches (about 10 cm to about 20 cm).

The second section 56 may or may not contain elastics 60 that extend transversely there across. By designing and manufacturing the absorbent article 10 to a ratio $L_2/L_3$, with a range of from between about 0.1 to about 2, one can improve the body fit of the absorbent article 10. Preferably, the ratio $L_2/L_3$ ranges from between about 0.2 to about 1.6, and more preferably, the ratio $L_2/L_3$ ranges from between about 0.3 to about 1.5. By manufacturing the back portion 14 to this desired ratio, one can improve the body fit of the disposable absorbent article 10 and minimize fluid leakage.

The second section 56 can have first and second leg elastics 62 and 64 that are aligned adjacent to first and second edges 66 and 68. Preferably, the line 58 will intersect at a point where the first and second edges 66 and 68 meet the first and second side edges 46 and 48, respectively. The leg elastics 62 and 64 can include one or more elastic strands, ribbons, bands or strips that are arranged approximately parallel to the edges 66 and 68 respectively. Preferably, there are from between about one to about six elongated elastic strands making up each leg elastic 62 and 64. Most preferably, each of the leg elastics 62 and 64 contains three elastic strands. The elastic strands can be aligned parallel to one another. For good results, the leg elastics 62 and 64 should be positioned inward about 1 inch (about 2.5 cm) from the first and second edges 66 and 68, respectively. More preferably, the leg elastics 62 and 64 should be positioned inward about 0.75 inches (about 2 cm)

from the first and second edges 66 and 68, respectively. Most preferably, the leg elastics 62 and 64 should be positioned inward about 0.5 inches (about 1.3 cm) from the first and second edges 66 and 68.

The leg elastics 62 and 64 are shown extending from the side edges 46 and 48 of the first section 54 to the second end 52 of the back portion 14. One should note that the exact location of the line 58 would dictate whether the leg elastics 62 and 64 are completely contained within the second section 56 or if they extend into the first section 54. The leg elastics 62 and 64 function to gather the material from which the back portion 14 is formed at a location adjacent to the leg openings which are formed as the front and back portions 12 and 14 are secured together to form a pant-like article. Various types of elastics can be used to form the leg elastics 62 and 64. The leg elastics 62 and 64 should have a tension of from between about 10 grams to about 400 grams. Preferably, the leg elastics 62 and 64 should have a tension of from between about 50 grams to about 220 grams. More preferably, the leg elastics 62 and 64 should have a tension of from between about 80 grams to about 200 grams.

Figure 4:
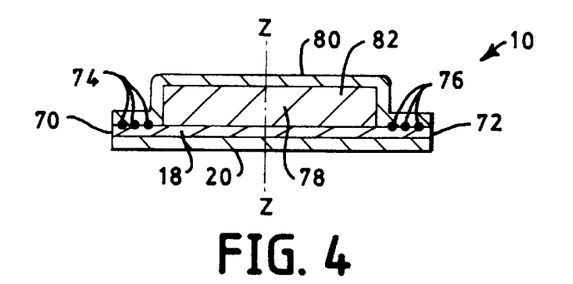
FIG. 4 is a cross-sectional view of FIG. 1 taken along the line 4—4.

Referring to FIGS. 1 and 4, the absorbent article 10 also includes the crotch portion 16. The crotch portion 16 connects the front portion 12 to the back portion 14. As noted above, the front portion, back portion and crotch portions can all be part of a single sheet of material. The crotch portion 16 has a first side edge 70 and a second side edge 72 and can have an hourglass, rectangular, square, oval or some other configuration. Each of the side edges 70 and 72 can be straight and aligned parallel or non-parallel to one another. The side edges 70 and 72 can also be curved, arcuate, irregular, convex or concave in shape. Preferably, the side edges 70 and 72 are arcuate in shape with the narrowest distance between the side edges 70 and 72 occurring along the transverse centerline Y—Y. The crotch portion 16 can be a single layer or a laminate as depicted. Since the crotch portion 16 acts as a baffle to body fluid that is absorbed by the absorbent article 10, it should be liquid-impermeable. If the crotch portion 16 is a laminate, at least one layer of the laminate should be liquid-impermeable. Polypropylene, polyethylene, or any other thermoplastic material works well as a liquid-impermeable layer. Preferably, the crotch portion 16 is a laminate formed from a layer of thermoplastic film and a layer of non-woven material. The non-woven material can be spunbond. Spunbond is a having an office at 401 North Lake Street, Neenah, Wis. 54956.

The crotch portion 16 can also include first and second crotch elastics 74 and 76. The crotch elastics 74 and 76 are located adjacent to the first and second side edges 70 and 72, respectively. The crotch elastics 74 and 76 are preferably contoured to match the profile of the side edges 70 and 72. The crotch elastics 74 and 76 are located inward about 1 inch (about 2.5 cm) of the first and second side edges 70 and 72, respectively. Preferably, the crotch elastics 74 and 76 are located inward about 0.75 inches (about 2 cm) of the first and second side edges 70 and 72, respectively. More preferably, the crotch elastics 74 and 76 are located inward about 0.5 inches (about 1.3 cm) of the first and second side edges 70 and 72, respectively.

The crotch elastics 74 and 76 should have a tension of from between about 10 grams to about 400 grams. Preferably, the crotch elastics 74 and 76 should have a tension of from between about 50 grams to about 220 grams. More preferably, the crotch elastics 74 and 76 should have a tension of from between about 80 grams to about 200 grams.

The crotch elastics 74 and 76 can include one or more elongated elastic strands, ribbons or strips. Preferably, each of said first and second crotch elastics 74 and 76 includes at least two strands of elastics, and more preferably, at least three strands of elastics. The strands of each of the crotch elastics 74 and 76 can be aligned parallel to one another or they can be aligned in a non-parallel relationship, if so desired. A parallel alignment is preferred. The strands of each of the crotch elastics 74 and 76 can be spaced fairly close together, for example, within a millimeter of each other. The exact spacing can be adjusted depending on the size of the article, the width of the crotch portion 16, the strength of the crotch elastics 74 and 76, the material from which the article is constructed, etc.

The crotch elastics 74 and 76 can be positioned and secured between the layers 18 and 20 forming the laminate from which the crotch portion 16 is formed. Alternatively, the crotch elastics 74 and 76 can be adhered to an upper surface 78 of the upper layer 18 of the laminate, see FIG. 4. Preferably, the first and second crotch elastics 74 and 76 are bonded to the upper surface 78 of the upper layer 18 by an adhesive.

Referring to FIGS. 1–4, the absorbent article 10 can include a liquid permeable liner 80. The liquid permeable liner 80 is also referred to as a bodyside cover. The liner 80 is not required but the absorbent article 10 will be described as including the liner 80. The liquid permeable liner 80, when present, can be formed from any natural or synthetic material that is liquid permeable. The liquid permeable liner 80 can also be formed from a non-woven material. Spunbond is a good material from which to construct the liquid permeable liner 80.

The liquid permeable liner 80 can be secured to at least one of the front, back or crotch portions 12, 14 or 16. The liquid permeable liner 80 is shown being directly attached to the crotch portion 16. Alternatively, the liquid permeable liner 80 can be indirectly attached to the crotch portion 16 via one or more layers. In this case, the intermediate layer would be secured to at least one of the front, back or crotch portions 12, 14 or 16. For example, the liquid permeable liner 80 can be secured to a liquid-impermeable baffle that is then adhesively secured to the crotch portion 16.

In FIG. 1, the periphery of the liquid permeable liner 80 and the periphery of the crotch portion 16 are shown to be coterminous. When the crotch elastics 74 and 76 are positioned on the upper surface 78 of the laminate, they can be adhesively secured to the liquid permeable liner 80 such that they are arranged adjacent to the side edges 70 and 72 of the crotch portion 16.

The absorbent article 10 further includes an absorbent 82 positioned below the liquid permeable liner 80. The absorbent 82 can be in direct contact with the upper layer 18 of the crotch portion 16. The absorbent 82 is designed to absorb body fluid, especially urine and can include one or more layers of absorbent material. The layers can be constructed of similar or different materials. Suitable materials for the absorbent 82 include cellulose, wood pulp fluff, rayon, cotton, and meltblown polymers such as polyester, polypropylene or coform. Coform is a meltblown air-formed combination of meltblown polymers, such as polypropylene, and absorbent staple fibers, such as cellulose. A preferred material is wood pulp fluff, for it is low in cost, relatively easy to form and has great absorbency. It should be noted that if two or more layers are utilized, that it is not necessary that all the layers be formed from the same material or have the same density.

The absorbent 82 can also be formed from a composite comprised of a hydrophilic material that can be formed from various natural or synthetic fibers, wood pulp fibers, regenerated cellulose or cotton fibers, or a blend of pulp and other fibers. A preferred material is airlaid tissue.

It is also possible and sometimes advantageous to insert a superabsorbent material into the absorbent 82 so as to increase its ability to absorb a large amount of fluid in relation to its own weight. Typical superabsorbents used in absorbent articles such as incontinence garments and diapers can absorb more than 10 times their weight in body fluid. The superabsorbent material can be inserted as particles, fibers or in sheet form. Hydroxyfunctional polymers have been found to be good superabsorbents for disposable absorbent articles. Such superabsorbents are commercially available from The Dow Chemical Company, Stockhausen, Inc., as well as other companies. Two such superabsorbents are DRYTECH® 2035 M and FAVOR® SXM 880. DRYTECH® is a registered trademark of The Dow Chemical Company having an office at 2030 Dow Center, Midland, Mich. 48642. FAVOR® is a registered trademark of Stockhausen, Inc. having an office at 2401 Doyle Street, Greensboro, N.C. 27406. The superabsorbent can be a partially neutralized salt of cross-linked copolymers of polyacrylic acid. Other types of superabsorbent materials known to those skilled in the art can also be used.

Figure 5:
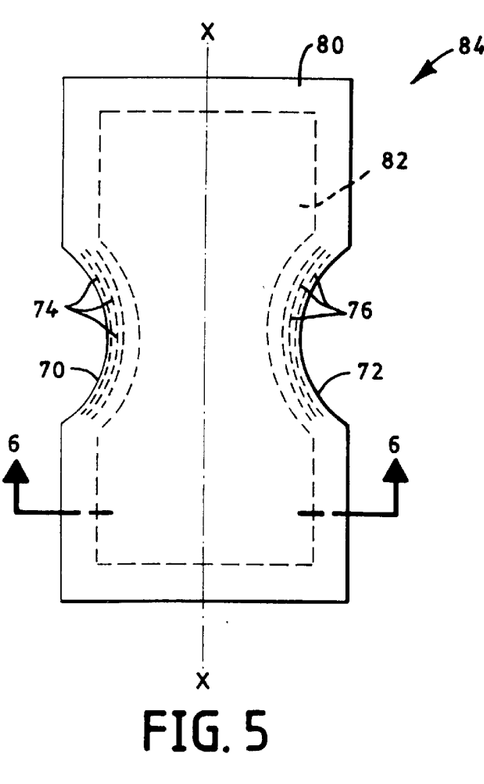
FIG. 5, is a top view of an alternative absorbent assembly.
Figure 6:
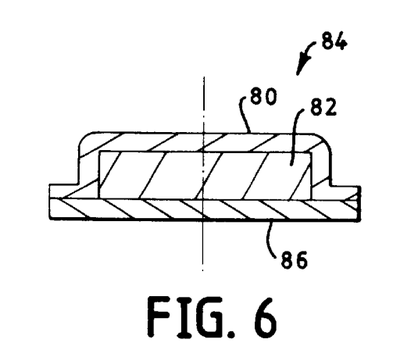
FIG. 6 is a cross-sectional view of FIG. 5 taken along line 6—6.

Referring to FIGS. 5 and 6, an absorbent assembly 84 is depicted which includes, from top to bottom, a liquid permeable bodyside liner 80, one or more layers of an absorbent 82 and a liquid-impermeable baffle 86. The liquid-impermeable baffle 86 can be formed from a thin layer of thermoplastic material such as polyethylene, polypropylene or other kinds of liquid-impermeable material. Preferably, the baffle 86 is formed from a liquid-impermeable film. It should be noted that the baffle could be formed from a laminate wherein at least one of the layers is liquid-impermeable.

In the absorbent assembly 84, the crotch elastics 74 and 76 are sandwiched between the liner 80 and the baffle 86. The crotch elastics 74 and 76 can be held in place by a glue, an adhesive, by ultrasonics, by heat, by pressure, by a combination of heat and pressure, or by some other bonding mechanism known to those skilled in the art. It is also possible to secure the crotch elastics 74 and 76 to the lower or exterior surface of the baffle 86 if desired. For good results, the crotch elastics 74 and 76 should be positioned within about 1 inch (about 2.5 cm) from the respective side edge 70 and 72. More preferably, the crotch elastics 74 and 76 should be positioned within about 0.75 inches (about 2 cm) from the respective side edge 70 and 72. Most preferably, the crotch elastics 74 and 76 should be positioned within about 0.5 inches (about 1.3 cm) from the respective side edge 70 and 72.

The absorbent assembly 84 can be placed or positioned on or over the crotch portion 16 of the absorbent article 10 and can be retained in place by an adhesive or some other type of fastener. Since the baffle 86 is liquid-impermeable, the crotch portion 16 would not have to be constructed from a liquid-impermeable material. The absorbent assembly 84 can be either permanently or releasably secured to at least one of the front, back or crotch portions 12, 14 or 16 of the absorbent article 10. Preferably, the absorbent assembly 84 is secured to the crotch portion 16 by an adhesive.

Figure 7:
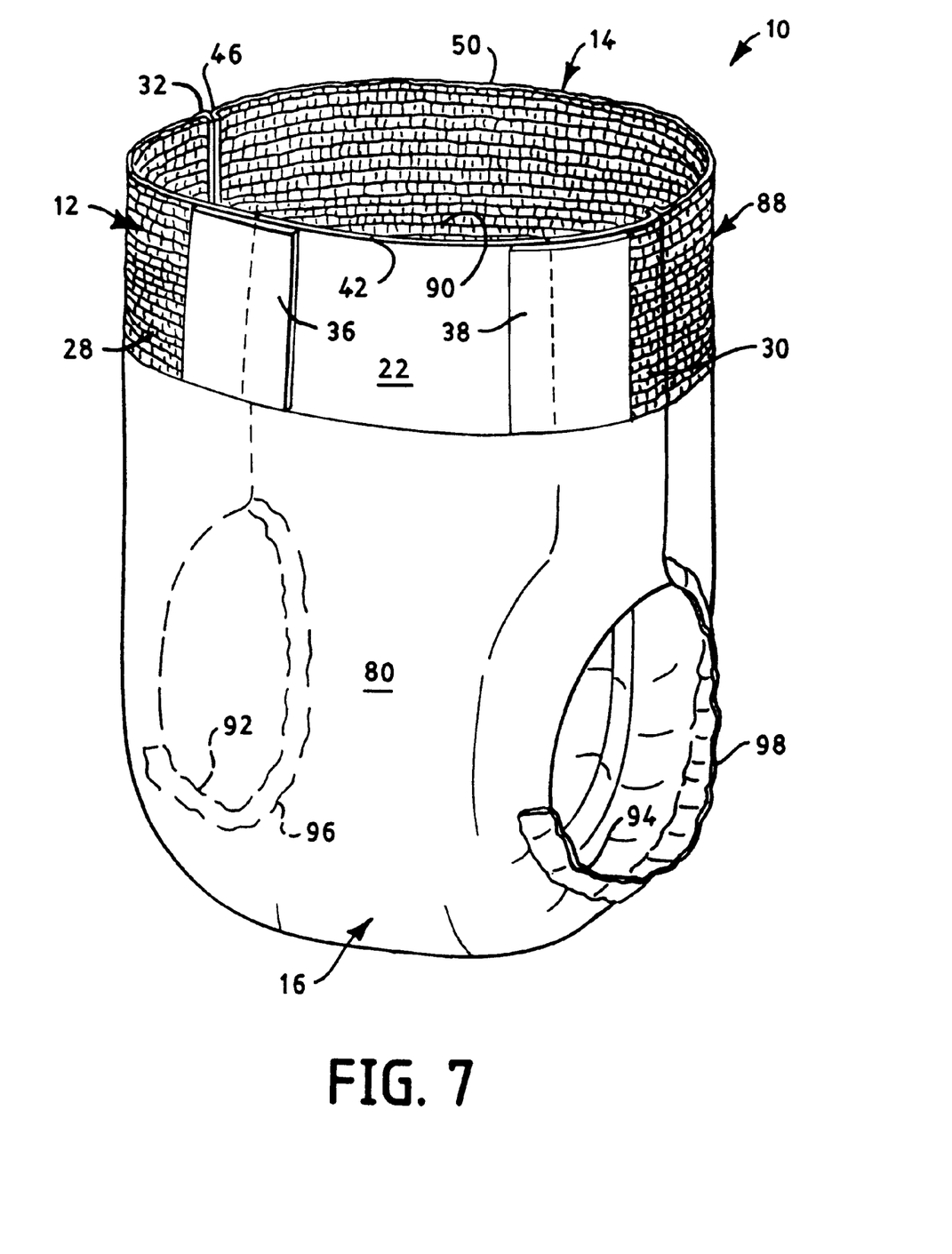
FIG. 7 is a perspective view of the "in use" configuration of the refastenable absorbent article shown in FIG. 1 once the front and back portions are secured together.

Referring now to FIGS. 1 and 7, each of the outer edges 32 and 34 of the first and second lateral sections 28 and 30, are securely attached to one of the first and second side edges 46 and 48 to form a pant-like article 88. The pant-like article 88 has a waist opening 90 and a pair of first and second leg openings 92 and 94. The leg elastic 62, the crotch elastic 74, and possibly the elastic first section 54 can cooperate to form gathers 96 around the first leg opening 92. Likewise, the leg elastic 64, the crotch elastic 76, and possibly the elastic first section 54 can cooperate to form gathers 98 around the second leg opening 94. It should be noted that the absorbent article 10 could be sold in the assembled condition, as is shown in FIG. 7 or with the lateral regions detached from the central or front portions.

Referring again to FIG. 1, the back portion 14 of the absorbent article 10 has been described with reference to a first section 54 and a second section 56. The first section 54 has a length $L_2$ and the second section 56 has a length $L_3$, both measured parallel to the longitudinal central axis X—X. The combination of the length $L_2$ and the length $L_3$ equals a new length $L_4$. The length $L_4$ should range from between about 3 inches (about 7.5 cm) to about 25 inches (about 64 cm). Preferably, for an adult size garment, the length $L_4$ should range from between about 7 inches to about 17 inches (about 18 cm to about 43 cm). Most preferably, for an adult size garment, the length $L_4$ should range from between about 10 inches to about 15 inches (about 25 cm to about 38 cm).

In addition, the absorbent article 10 has an overall length $L_5$ measured perpendicularly from the first end 42 of the front portion 12 to the first end 50 of the back portion 14. The length $L_5$ should range from between about 10 inches (about 25 cm) to about 45 inches (about 114 cm). Preferably, for an adult size garment, the length $L_5$ should range from between about 20 inches (about 51 cm) to about 40 inches (about 102 cm). Most preferably, for an adult size garment, the length $L_5$ should range from between about 30 inches (about 76 cm) to about 35 inches (about 89 cm).

A ratio $L_4/L_5$ can be established which ranges from between about 0.1 to about 0.5. Preferably, the ratio $L_4/L_5$ ranges from between about 0.2 to about 0.5 and more preferably, the ratio $L_4/L_5$ ranges from between about 0.3 to about 0.4. By designing and manufacturing the absorbent article 10 to fit within the values established for the ratio $L_4/L_5$, one can be confident that the absorbent article 10 will exhibit improved body fit and be less likely to leak body fluid.

Returning again to the front portion 12 depicted in FIG. 1, it was mentioned that the front portion 12 had a length $L_1$. Since the front portion 12 is designed to mate with the back portion 14, it is advantageous to size the length $L_1$ to be approximately equal to the length $L_2$. This will provide an aesthetically pleasing pant-like article 88. However, if one desires, the length $L_1$ could be sized to be less than, equal to or greater than the length $L_2$.

Figure 8:
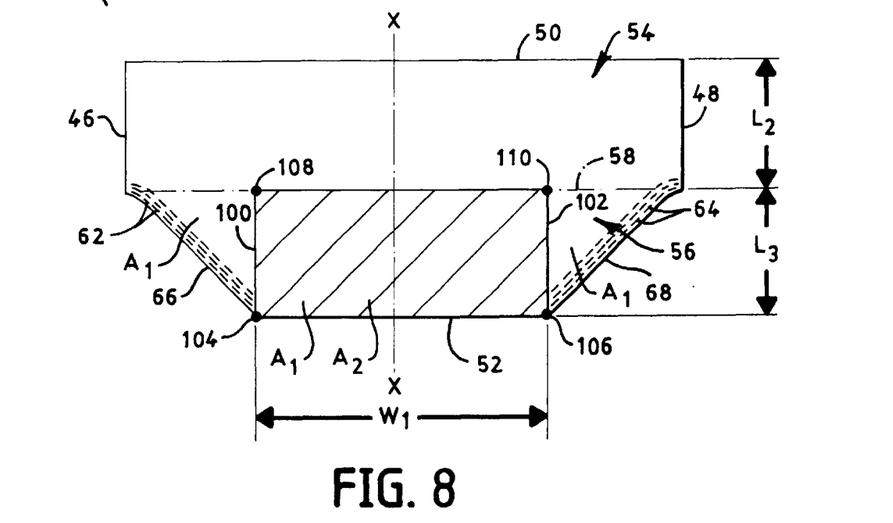
FIG. 8 is a top view of the back portion of the absorbent article with the elastic removed for clarity and showing one way to measure a ratio $A_1/A_2$ for the second section for obtaining improved body fit.

Referring now to FIG. 8, the back portion 14 of the absorbent article 10 is depicted with the elastic 60 removed for clarity of discussion only. The back portion 14, as described above, has a first section 54 and a second section 56. The first section 54 has a length $L_2$ that is equal to or greater than about 2 inches (about 5 cm) and the second section 56 has a length $L_3$ that is equal to or greater than about 1 inch (about 2.5 cm). The second section 56 includes a first area $A_1$ and a second area $A_2$. The first area $A_1$ is bounded by the second end 52, the line 58 drawn parallel to the first end 50, and the first and second side edges 66 and 68. In essence, the first area $A_1$ represents the total area of the second section 56. The second area $A_2$ is depicted as the cross hatched area bounded by first and second lines 100 and 102, the second end 52, and the line 58 drawn parallel to the first end 50. The first and second lines 100 and 102 are drawn perpendicular to the second end 52 at points 104 and 106 where the first and second side edges 66 and 68 intersect the second end 52. The first and second lines 100 and 102 extend vertically upward and intersect the line 58 at points 108 and 110, respectively. It has been found that if one divides the first area $A_1$ by the second area $A_2$, a ratio $A_1/A_2$ is established. If this ratio $A_1/A_2$ is maintained within a certain limited range, one can manufacture a disposable absorbent article 10 that exhibits improved body fit in the buttocks region of the wearer. Such improved body fit reduces the likelihood of fluid leakage from occurring which is of utmost importance to a consumer of such products.

The first area $A_1$ should be equal to or greater than about 175 $cm^2$. Preferably, for an adult size garment, the first area $A_1$ ranges from between about 400 $cm^2$ to about 1500 $cm^2$ More preferably, for an adult size garment, the first area A, ranges from between about 500 $cm^2$ to about 1200 $cm^2$. Most preferably, for an adult size garment, the first area $A_1$ ranges from between about 600 $cm^2$ to about 1100 $cm^2$. The second area $A_2$ should be equal to or greater than about 50 $cm^2$. The ratio $A_1/A_2$ should range from between about 1.3 to about 3.5. Preferably, the ratio $A_1/A_2$ should range from between about 1.7 to about 2.5, and more preferably, the ratio $A_1/A_2$ should range from between about 2.0 to about 2.3.

It should be noted that the first and second lines 100 and 102 are aligned parallel to one another and are spaced apart a distance denoted as $W_1$. $W_1$ represents the width of the second area $A_2$. The width $W_1$ should be equal to or greater than about 4 inches (about 10 cm). Preferably, the width $W_1$ should range from between about 5 inches (about 13 cm) to about 15 inches (about 38 cm), and more preferably, the width $W_1$ should range from between about 6 inches (about 15 cm) to about 11 inches (about 28 cm). The dimension $W_1$ can vary depending upon the type and size of absorbent article that is produced, as well as the age and physical size of the wearer. If the absorbent article is sized to be worn by an infant, the dimension $W_1$ will be less than if the absorbent article is designed to be worn by a toddler or by an adult. The gender of the wearer can also affect the dimension $W_1$.

Figure 9:
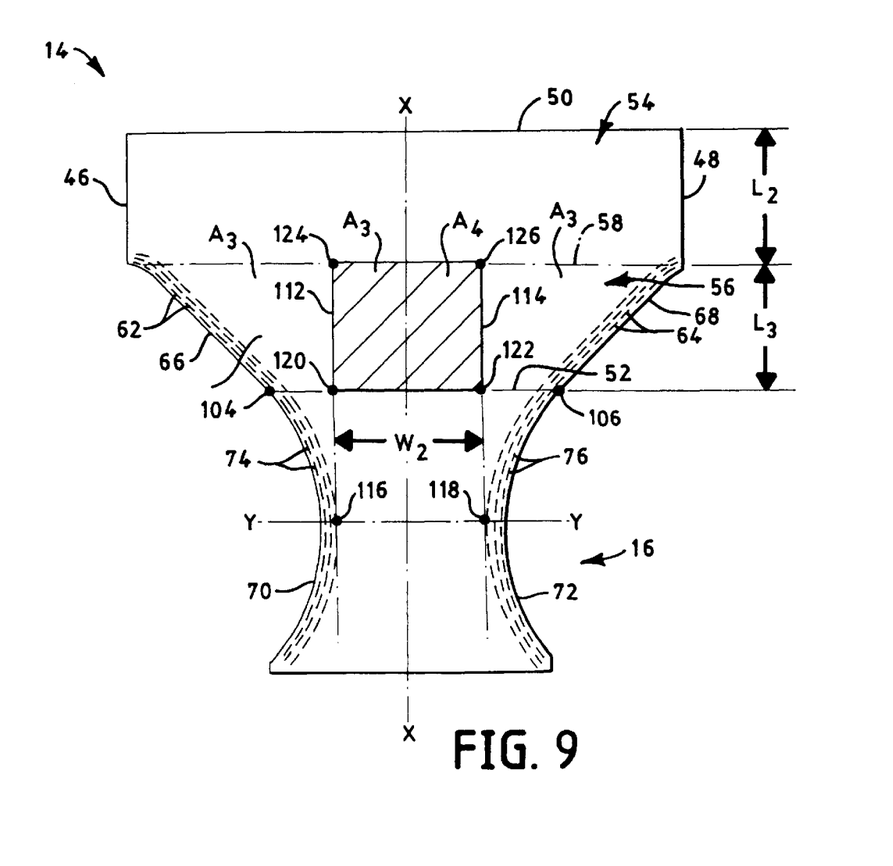
FIG. 9 is a top view of the back portion and crotch portion of the absorbent article with the elastic removed for clarity and showing an alternative way to measure a ratio $A_3/A_4$ for the second section for obtaining improved body fit.

Referring to FIG. 9, the back portion 14 and the crotch portion 16 of the absorbent article 10 are depicted with the elastic 60 removed from the back portion 14 for clarity of discussion only. The crotch portion 16 is joined at one end to the front portion 12, see FIG. 1. The crotch portion 16 has first and second side edges 70 and 72 and first and second crotch elastics 74 and 76 positioned adjacent to the first and second side edges 70 and 72. The back portion 14 is joined to the opposite end of the crotch portion 16, see FIG. 1. The back portion 14 has a first section 54 and a second section 56. The first section 54 has a length $L_2$ that is equal to or greater than about 2 inches (about 5 cm) and the second section 56 has a length $L_3$ that is equal to or greater than about 1 inch (about 2.5 cm). The second section 56 includes a first area $A_3$ and a second area $A_4$. The first area $A_3$ is bounded by the second end 52, the line 58 drawn parallel to the first end 50, and the first and second side edges 66 and 68. In essence, the first area [$A_1$] $A_3$ represents the total area of the second section 56. The second area [$A_2$] $A_4$ is depicted as the crosshatched area bounded by first and second lines 112 and 114, the second end 52, and the line 58 drawn parallel to the first end 50. The first and second lines 112 and 114 are drawn tangential to the first and second crotch elastics 74 and 76 at points 116 and 118 where the first and second crotch elastics are spaced closest together. Another way of stating this is that the first and second lines 112 and 114, respectively, are aligned tangentially to the inner most elastic strand of each of the first and second crotch elastics 74 and 76. For a symmetrically shaped article 10, this will occur on the transverse centerline Y—Y.

The first and second lines 112 and 114 extend vertically upward toward the first end 50 and intersect both the second end 52 at points 120 and 122, and the line 58 drawn parallel to the first end 50 at points 124 and 126. The crosshatched area bounded by the points 120, 122, 124 and 126 represent the second area $A_4$. It has been found that if one divides the first area $A_3$ by the second area $A_4$, that a ratio $A_3/A_4$ is established. If this ratio $A_3/A_4$ is maintained within a certain limited range, one can manufacture an absorbent article that exhibits improved body fit in the buttocks region of the wearer. Such improved body fit reduces the likelihood of fluid leakage from occurring which is of utmost importance to a disposable absorbent article.

The first area $A_3$ should be equal to or greater than about 175 $cm^2$. Preferably, the first area $A_3$ should range from between about 400 $cm^2$ to about 1500 $cm^2$. More preferably, the first area $A_3$ should range from between about 500 $cm^2$ to about 1200 $cm^2$, and most preferably, the first area $A_3$ ranges from between about 600 $cm^2$ to about 1100 $cm^2$. The second area $A_4$ should be equal to or greater than about 35 $cm^2$. The ratio $A_3/A_4$ should range from between about 1.5 to about 5.0. Preferably, the ratio $A_3/A_4$ should range from between about 2.5 to about 4.0, and more preferably, the ratio $A_3/A_4$ should range from between about 3.0 to about 3.7.

It should be noted that the first and second lines 112 and 114 are aligned parallel to one another and are spaced apart a distance denoted as $W_2$. $W_2$ represents the width of the second area $A_4$. The width $W_2$ should be equal to or greater than about 2 inches (about 5 cm). Preferably, the width $W_2$ should range from between about 3 inches (about 8 cm) to about 7 inches (about 18 cm), and more preferably, the width $W_2$ should range from between about 4 inches (about 10 cm) to about 6 inches (about 15 cm). The dimension $W_2$ can vary depending upon the type and size of absorbent article that is produced, as well as the age and physical size of the wearer. If the absorbent article is sized to be worn by an infant, the dimension $W_2$ will be less than if the absorbent article is designed to be worn by a toddler or by an adult. The gender of the wearer can also affect the dimension $W_2$.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations that fall within the spirit and scope of the appended claims.

We claim:

1. A refastenable absorbent having a longitudinal axis article comprising:

a) a front portion having a central section including first and second side edges, first and second lateral sections each positioned adjacent to one of said first and second side edges and each of said first and second lateral sections being releasably attached to said central section, each of said lateral sections having an outer edge, and said front portion having a first end and a second end;

b) a crotch portion connecting said front portion to a back portion: said crotch portion having a first side edge and a second side edge, each of said first and second side edges of said crotch portion having an end point adjacent said back portion; said end points located where a line drawn parallel to said longitudinal axis, at a maximum distance transversely from said longitudinal axis, passes through said first and second side edges of said crotch portion at least twice;

c) said back portion being divided into a first section and a second section; said first section bounded by a first end, a line drawn parallel to said first end, a first side edge, and a second side edge; said second section bounded by said line drawn parallel to said first end, a second end, a first edge. and a second edge; said line drawn parallel to said first end intersecting a pair of corners where said first and second side edges of said first section intersect with said first and second edges of said second section; said second end parallel to said first end and intersecting said end points where said first and second side edges of said crotch portion intersect with said first and second edges of said second section; said first section having a length $L_2$ measured perpendicularly from said first end to said line drawn parallel thereto; said second section having a length $L_3$ measured perpendicularly from said line drawn parallel to said first end to said second end; and said back portion having a ratio $L_2/L_3$ ranging from between about 0.2 to about 1.6; and d) an absorbent secured to at least one of said front, back or crotch portions, and each of said outer edges of said first and second lateral sections of said front portion being secured to one of said first and second side edges of said back portion to form a pant-like article having a waist opening and a pair of leg openings.

2. The refastenable absorbent article of claim 1 wherein said front portion has a length $L_1$ measured perpendicularly from said first end of said front portion to said second end of said front portion and $L_1$ is approximately equal to said $L_2$.

3. The refastenable absorbent article of claim 2 wherein said first section is elastic.

4. The refastenable absorbent article of claim 1 wherein $L_2$ is greater than about 2 inches.

5. The refastenable absorbent article of claim 1 wherein $L_2$ ranges from between about 4 inches to about 7 inches.

6. The refastenable absorbent article of claim 1 wherein said absorbent article includes a liner, said crotch portion has first and second side edges and elastic is secured between said liner and said crotch portion adjacent to said first and second side edges.

7. The refastenable absorbent article of claim 1 wherein each of said first and second lateral sections of said front portion contain elastic.

8. The refastenable absorbent article of claim 1 wherein said lengths $L_2$ and $L_3$ when added together equal a length $L_4$, and said absorbent article has an overall length $L_5$ measured from said first end of said front portion to said first end of said back portion, and a ratio $L_4/L_5$ is established which ranges from between about 0.1 to about 0.5.

9. The refastenable absorbent article of claim 8 wherein said ratio $L_4/L_5$ ranges from between about 0.2 to about 0.5.

10. A refastenable absorbent article having a longitudinal axis comprising:

a) a front portion having a central section including first and second side edges, first and second lateral sections each positioned adjacent to one of said first and second side edges and each of said first and second lateral sections being releasably attached to said central section, each of said lateral sections having an outer edge, and said front portion having a first end and a second end; said back portion being divided into a first section and a second section, b) a crotch portion connecting said front portion to said back portion having a first side edge and a second side edge, each of said first and second side edges of said crotch portion having an end point adjacent said back portion; said end points located where a line drawn parallel to said longitudinal axis, at a maximum distance transversely from said longitudinal axis, passes through said first and second side edges of said crotch portion at least twice;

c) said back portion being divided into a first section and a second section: said first section bounded by a first end, a line drawn parallel to said first end, a first side edge, and a second side edge: said second section bounded by said line drawn parallel to said first end, a second end, a first edge, and a second edge; said line drawn parallel to said first end intersecting a pair of corners where said first and second side edges of said first section intersect with said first and second edges of said second section; said second end parallel to said first end and intersecting said end points where said first and second side edges of said crotch portion intersect with said first and second edges of said second section; said first section having a length $L_2$ measured perpendicularly from said first end to said line drawn parallel thereto; said second section having a length $L_3$ measured perpendicularly from said line drawn parallel to said first end to said second end; and said back portion having a ratio $L_2/L_3$ ranging from between about 0.3 to about 1.5;

d) a liquid permeable liner secured to at least one of said front, back or crotch portions; and e) an absorbent positioned below said liner, and each of said outer edges of said first and second lateral sections of said front portion being secured to one of said first and second side edges of said back portion to form a pant-like article having a waist opening and a pair of leg openings, wherein said lengths $L_2$ and $L_3$ when added together equal a length $L_4$ and said absorbent article has an overall length $L_5$ measured from said first end of said front portion to said first end of said back portion, and a ratio $L_4/L_5$ is established which ranges from between about 0.1 to about 0.5.

11. The refastenable absorbent article of claim 10 wherein said front portion has a length $L_1$ measured perpendicularly from said first end of said front portion to said second end of said front portion and $L_1$ is approximately equal to said $L_2$.

12. The refastenable absorbent article of claim 10 wherein each of said first and second lateral sections of said front portion contain elastic.

13. The refastenable absorbent article of claim 10 wherein said ratio $L_4/L_5$ ranges from between about 0.2 to about 0.5.

14. The refastenable absorbent article of claim 10 wherein said ratio $L_4 L_5$ ranges from between about 0.3 to about 0.4.

15. A refastenable absorbent article having a longitudinal axis comprising:

a) a front portion having a central section including first and second side edges, first and second lateral sections each positioned adjacent to one of said first and second side edges and each of said first and second lateral sections being releasably attached to said central section by a hook and loop fastener, each of said lateral sections having an outer edge, and said front portion having a first end and a second end;

b) a crotch portion connecting said front portion to a back portion; said crotch portion having a first side edge and a second side edge, each of said first and second side edges of said crotch portion having an end point adjacent said back portion; said end points located where a line drawn parallel to said longitudinal axis, at a maximum distance transversely from said longitudinal axis, passes through said first and second side edges of said crotch portion at least twice;

c) said back portion being divided into a first section and a second section: said first section bounded by a first end, a line drawn parallel to said first end. a first side edge, and a second side edge; said second section bounded by said line drawn parallel to said first end, a second end, a first edge, and a second edge; said line drawn parallel to said first end intersecting a pair of corners where said first and second side edges of said first section intersect with said first and second edges of said second section; said second end parallel to said first end and intersecting said end points where said first and second side edges of said crotch portion intersect with said first and second edges of said second section; said first section having a length $L_2$ measured perpendicularly from said first end to said line drawn parallel thereto; said second section having a length $L_3$ measure perpendicularly from said line drawn parallel to said first end to said second end; and said back Portion having a ratio $L_2/L_3$ ranging from between about 0.2 to about 1.6;

d) a liquid permeable liner secured to at least one of said front, back or crotch portions; and e) an absorbent positioned below said liner, and each of said outer edges of said first and second lateral edges of said front portion being secured to one of said first and second side edges of said back portion to form a pant-like article having a waist opening and a pair of leg openings, wherein said lengths $L_2$ and $L_3$ when added together equal a length $L_4$ and said absorbent article has an overall length $L_5$ measured from said first end of said front portion to said first end of said back portion, and a ratio $L_4/L_5$ is established which ranges from between about 0.2 to about 0.5.

16. The refastenable absorbent article of claim 15 wherein said front portion has a length $L_1$ measured perpendicularly from said first end of said front portion to said second end of said front portion, and $L_1$ is approximately equal to said $L_2$.

17. The refastenable absorbent article of claim 15 wherein each of said lateral sections is releasably attached to said central section by a hook and loop fastener.

18. The refastenable absorbent article of claim 15 wherein said ratio $L_2/L_3$ ranges from between about 0.3 to about 1.5.

19. The refastenable absorbent article of claim 15 wherein said ratio $L_4/L_5$ ranges from between about 0.3 to about 0.4.

20. The refastenable absorbent article of claim 15 wherein said crotch portion has first and second side edges and elastic is secured between said liner and said crotch portion adjacent to said first and second side edges.

* * * * *

UNITED STATES PATENT AND TRADEMARK OFFICE
CERTIFICATE OF CORRECTION

PATENT NO.    : 6,503,239 B1
DATED         : January 7, 2003
INVENTOR(S)   : Mary Anne Bruemmer-Prestley et al.

It is certified that error appears in the above-identified patent and that said Letters Patent is hereby corrected as shown below:

Column 10,
Line 53, insert -- article -- after "absorbent".
Line 54, delete "article" after "axis".

Column 12,
Line 54, insert -- / -- after "$L_4$".

Signed and Sealed this

Seventeenth Day of February, 2004

JON W. DUDAS
*Acting Director of the United States Patent and Trademark Office*